United States Patent
Weiβ et al.

(10) Patent No.: US 8,673,367 B2
(45) Date of Patent: Mar. 18, 2014

(54) NANO SILVER-ZINC OXIDE COMPOSITION

(75) Inventors: Thomas Weiβ, Ilvesheim (DE); Rainer Xalter, Basel (CH)

(73) Assignee: Polymers CRC Ltd., Notting Hill Vic (AU)

( * ) Notice: Subject to any disclaimer, the term of this patent is extended or adjusted under 35 U.S.C. 154(b) by 9 days.

(21) Appl. No.: 13/391,655

(22) PCT Filed: Aug. 16, 2010

(86) PCT No.: PCT/EP2010/061900
§ 371 (c)(1),
(2), (4) Date: Mar. 27, 2012

(87) PCT Pub. No.: WO2011/023584
PCT Pub. Date: Mar. 3, 2011

(65) Prior Publication Data
US 2012/0177713 A1   Jul. 12, 2012

(30) Foreign Application Priority Data
Aug. 27, 2009  (EP) ..................... 09168776

(51) Int. Cl.
*A01N 59/16*  (2006.01)
*A61K 33/38*  (2006.01)

(52) U.S. Cl.
CPC ............... *A61K 33/38* (2013.01); *A01N 59/16* (2013.01); *A61L 2300/104* (2013.01)
USPC ............ 424/618; 424/405; 424/641; 424/635

(58) Field of Classification Search
None
See application file for complete search history.

(56) References Cited

U.S. PATENT DOCUMENTS

| | | | |
|---|---|---|---|
| 4,609,525 A * | 9/1986 | Schreiner et al. | 419/6 |
| 5,973,068 A * | 10/1999 | Yamaya et al. | 524/865 |
| 2004/0259973 A1* | 12/2004 | Sakuma et al. | 523/122 |
| 2007/0012189 A1 | 1/2007 | Kang et al. | |
| 2009/0130161 A1 | 5/2009 | Sarangapani | |
| 2011/0024355 A1 | 2/2011 | Mansouri | |
| 2011/0266507 A1 | 11/2011 | Fuchs | |
| 2011/0288206 A1 | 11/2011 | Fuchs | |
| 2011/0294920 A1 | 12/2011 | Fuchs | |
| 2012/0108712 A1 | 5/2012 | Xalter | |

FOREIGN PATENT DOCUMENTS

| | | |
|---|---|---|
| CN | 1759682 A | 4/2006 |
| CN | 1771807 A | 5/2006 |
| EP | 1743691 A1 | 1/2007 |
| WO | 2009047154 A1 | 4/2009 |

OTHER PUBLICATIONS

English language abstract of CN 101053782, Oct. 17, 2007.
Kumar et al., Water Science and Technology, vol. 59, No. 7, Jul. 2009 pp. 1423-1430.
Oana et al., Semiconductor Conference, 2007, CAS 2007 pp. 315-318.
Zhou et al., Materials Science in Seminconductor Processing, vol. 10, No. 2-3, Apr. 1, 2007, pp. 90-96.
Lu et al., Nanotechnology 20081105 GB, vol. 19, No. 44, Sep. 30, 2008, pp. 1-10.
Bhattacharyya et al., Journal of Physical Chemistry C, vol. 112, No. 3, Dec. 28, 2007, pp. 659-665.
Shvalagin et al., Journal of Nanoparticle Research, vol. 9, No. 3, Jul. 19, 2006, pp. 427-440.
Deng et al., Nanotechnology, vol. 20, No. 17, Apr. 29, 2009, p. 175705.
Copending U.S. Appl. No. 13/384,772, filed Jan. 19, 2012.
Eng. language abst of CN1771807 May 17, 2006.
Eng. language abst of CN1759682 Apr. 19, 2006.

* cited by examiner

*Primary Examiner* — Bethany Barham
(74) *Attorney, Agent, or Firm* — Tyler A. Stevenson

(57) ABSTRACT

A new composite comprises (a) 10.1-99.9% by weight of elemental Ag and (b) 0.1-89.9% by weight of ZnO, wherein the sum of (a) and (b) makes 90% or more by weight of the composite and wherein the elemental Ag has a primary particle size of 10-200 nm and/or the ZnO has a primary particle size of 0.1 to below 50 μm and/or the composite has a particle size distribution of 0.1-50 μm and/or a BET surface area of 10-100 m2/g. The novel composite may be obtained by the steps (i) mixing a first mixture of at least one Ag-salt with a second mixture of at least one Zn-salt thereby forming a third mixture of Ag- and Zn-salts, (ii) adding the third mixture to a mixture of a carbonate source, (iii) co-precipitating of the Ag- and Zn-carbonates formed in step (ii), (iv) washing of the Ag- and Zn-carbonates and (v) thermal decomposing of the Ag- and Zn-carbonates. The novel composites are useful to impart antimicrobial properties to surfaces, articles or bulk compositions, especially to membrane systems for gas- or water separation.

14 Claims, No Drawings

NANO SILVER-ZINC OXIDE COMPOSITION

The present invention relates to silver/zinc oxide based composites, their manufacturing process, antimicrobial membranes comprising these composites and the use of such membranes in water purification systems which may be exposed to microbial contamination.

It is known that silver-based antimicrobials limit the growth of microbes by multiple effects. Unlike antibiotics, silver is toxic to multiple components of bacterial cell metabolism. These include damage to the bacterial cell wall and membrane permeability leads to gross cellular structural changes, blockage of transport and enzyme systems such as the respiratory cytochromes, alteration of proteins and binding of microbial deoxyribonucleic acid and ribonucleic acid to prevent transcription and division. Typically, the toxicity of silver ions for mammal cells are much lower compared to protozoan cells of e.g. bacteria, algae, yeast. This makes silver highly attractive as non-specific biocide especially for application with water contact even drinking water applications where no restrictions are given for silver ions in the range of ppm concentration. Typically strong effects are observed in concentrations of 40-160 ppm Ag.

It is known that polymers and plastics, e.g. when used as coatings on substrates, can suffer from bacterial or algal decay if routinely exposed to water, dampness or moisture. Biofilms of communities of bacteria and algae can settle on the surfaces of these substrates and increase the speed of decay and/or loss of efficacy.

Bacteria contained in the influent water are accumulated by the membranes and consequently accumulate on their surfaces. The rapid growth of bacteria results in fouling of the membrane which reduces the flow of water through the membrane and can adversely affect the filtering properties of the membrane.

As a result of bacterial growth on the membrane, a gelatinous biofilm is formed on the upstream side of membrane that is very difficult to remove except through the use of aggressive cleaning. This can compromise membrane lifetime as well as incur significant costs.

CN 101053782 describes an antibacterial cellulose acetate nanofiltration membrane and the preparation thereof by chemical surface modification of antibacterial nano-particles like titanium dioxide, zinc oxide, silver powder or powdered copper in a plasma reaction chamber and preparation of a casting membrane solution comprising cellulose acetate and the chemically modified antibacterial nano-particles. Furthermore, in Water Research, (2008), 42(18), 4591-4602, antimicrobial materials in form of nano-scale silver and zinc oxide for water disinfection and microbial control are described.

Thus, a need for membranes with long-term antimicrobial activities exists.

It has now surprisingly found that a composite of elemental nano-scale silver in micro-scale zinc oxide with a high surface provides improved antimicrobial properties.

It is therefore an object of the present invention to provide a composite comprising, preferably consisting of, (a) 10.1-99.9% by weight of elemental silver (Ag) and (b) 0.1-89.9% by weight of zinc oxide (ZnO),
whereby the sum of (a) and (b) makes 90% or more by weight of the composite and wherein the elemental silver has a primary particle size of 10-200 nm and/or the zinc oxide has a primary particle size of 0.1 to below 50 µm and/or the composite has a particle size distribution of 0.1-50 µm and/or a BET surface area of 10-100 $m^2/g$.

In a preferred embodiment of the invention the elemental silver of the composite has a primary particle size of 10-100 nm, preferably 30-80 nm.

Preferably the zinc oxide of the composite has a primary particle size of 0.1 to below 30 µm, preferably 0.1 to below 22 µm, more preferably 1 to below 22 µm.

In a preferred embodiment of the invention the composite has a particle size distribution of 1-30 µm, preferably 1-22 µm.

The BET surface area of the composite of the present invention is preferably 20-80 $m^2/g$, more preferably 35-45 $m^2/g$.

Preferably the composite according to the invention comprises (a) 20.1-99.9% by weight of elemental silver and (b) 79.9-0.1% by weight of zinc oxide, more preferred (a) 20.1-40.0% by weight of elemental silver and (b) 79.9-60.0% by weight of zinc oxide, whereby the sum of (a) and (b) makes 90% or more by weight of the composite.

Preferably the sum of (a) and (b) makes 95% or more, more preferably 100% by weight of the composite.

According to the present invention the method to be used to determine the primary particle size is SEM (Scanning Electron Microscope). By using a combined method of EDX (Energy Dispersive X-ray spectroscopy) additional information about the elemental constitution of a smallest sample area (nm scale) is possible. Furthermore, the particle size distribution according to the present invention is measured by laser granulometry (Laser diffraction measurement method, whereby the primary source of information used to calculate the particle size is the map of scattering intensity versus angle). The specific surface area is measured using nitrogen and the BET method according to ISO 9277.

The composite according to the invention can preferably be obtained by thermal decomposition of suitable silver/zinc precursor compounds. More preferably, the composite according to the invention is obtained by thermal decomposition of suitable silver/zinc precursor compounds as described in the following.

A further object of the present invention is to provide a method (process) wherein silver- and zinc-carbonates are co-precipitated in one step from the corresponding mixtures of silver/zinc salts solutions followed by a thermal decomposition of the carbonates formed.

The novel composite may be obtained by a process comprising the steps of
(i) mixing a first mixture of at least one silver-salt (Ag-salt) with a second mixture of at least one zinc-salt (Zn-salt) thereby forming a third mixture of silver- and zinc-salts,
(ii) adding the third mixture to a mixture of a carbonate source,
(iii) co-precipitating of the silver- and zinc-carbonates formed in step (ii),
(iv) washing of the silver- and zinc-carbonates and
(v) thermal decompositing of the silver- and zinc-carbonates.

In the method of the invention any silver-salt known to a person skilled in the art to be suited to be mixed with a zinc-salt may be used. The same applies for the zinc-salts.

Preferred silver-salts are selected from the group consisting of silver-nitrate, silver-acetate, silver-sulfate, silver-citrate, silver-methanesulfonate, silver-fluoride, silver-lactate, silver-behenate, silver-bromate, silver-carbonate, silver-citrate, silver-cyanide, silver-cyclohexanebutyrate, silver diethyldithiocarbamate, silver-hexafluoroantimonate, silver-hexafluoroasenate, silver-hexafluorophosphate, silver-hydrogenfluorid, silver-methansulfonate, silver-nitrite, silver-perchlorate, silver-phosphate, silver-potassium-cyanide, silver-postassium-jodide, silver-salicylate, silver-stearate, silver-sulfite, silver-tetrafluoroborate, silver-thiocyanate, silver-p-toluenesulfonate, silver-trifluoroacetate, silver-trifluoromethansulfonate, silver-sulfamate, silver-formate, silver-oxalate, silver-nitrite and mixtures thereof. In a more preferred embodiment the silver-salts are selected from the group consisting of silver-nitrate, silver-acetate, silver-sulfate, silver-citrate, silver-methanesulfonate, silver-fluoride and mixtures thereof. In an especially preferred embodiment silver-nitrate is used.

Preferred zinc-salts are selected from the group consisting of zinc-nitrate, zinc-acetate, zinc-sulfate, zinc-citrate, zinc-methanesulfonate, zinc-chloride, zinc-bromide, zinc-iodide, zinc-fluoride, zinc-lactate, zinc-behenate, zinc-undecylenate, zinc-bromate, zinc-carbonate, zinc-citrate, zinc-cyanide, zinc-diethyldithiocarbamate, zinc-hexafluoroantimonate, zinc-hexafluoroasenate, zinc-haxafluorophosphate, zinc-hexafluorosilicate, zinc-methansulfonate, zinc-nitrite, zinc-perchlorate, zinc-phosphate, zinc-potassium-cyanide, zinc-salicylate, zinc-stearate, zinc-sulfite, zinc-tetrafluoroborate, zinc-thiocyanate, zinc-p-toluenesulfonate, zinc-benzolsulfinate, zinc-trifluoroacetate, zinc-trifluoromethansulfonate, zinc-sulfamate, zinc-formiate, zinc-nitrite, zinc-oxalate and mixtures thereof. In a more preferred embodiment the zinc-salts are selected from the group consisting of zinc-nitrate, zinc-acetate, zinc-sulfate, zinc-citrate, zinc-methanesulfonate, zinc-chloride, zinc-bromide, zinc-iodide and mixtures thereof. In an especially preferred embodiment zinc-nitrate is used.

As solvent for the mixtures of the silver- and zinc-salts of step (i) any solvent can be used which is suited to dissolve the corresponding silver- and zinc-salts. Preferred solvents are selected from the group consisting of aqueous solvents, alcohols, ketones, ethers, esters, organic carbonates, organic amines, ionic liquids and mixtures thereof, preferably in combination with surface active substances. In a preferred embodiment water is used as solvent.

The mixing of the silver- and zinc-salts can be carried out by separately dissolving the respective silver- and zinc-salts and subsequent mixing of the mixtures formed. Alternatively the mixing and dissolving of the respective silver- and zinc-salts can be carried out simultaneously. The temperature for dissolving the respective silver- and zinc-salts is preferably from 5 to 100° C., more preferably from 25 to 80° C. The molar ratio of the silver- and zinc-salts is generally chosen to fit with the desired composition of the composite, i.e. 10.1-99% by weight of elemental silver and 0.1-89.9% by weight of ZnO, thus often corresponding to about 1-92 molar parts of silver on about 110 to 0.1 molar parts of zinc in the educt salt mixture; especially about 19-37 molar parts of silver on about 98 to 74 molar parts of zinc in the educt salt mixture. The concentration of the silver- and zinc-salts is independently from each other preferably in the range of 0.1-5 M depending on the final silver/zinc oxide ratio.

Suitable carbonate sources in step (ii) are preferably selected from the group consisting of carbonic acid, ammonium carbonate, guanidinium carbonate, potassium carbonate, sodium carbonate, lithium carbonate, the corresponding hydrogen carbonates and mixtures thereof; preferably potassium carbonate is used.

The solvents for the mixture of the carbonate source are preferably selected from the group consisting of aqueous solvents, alcohols, ketones, ethers, esters, organic carbonates, organic amines, ionic liquids and mixtures thereof, preferably in combination with surface active substances. In a preferred embodiment water is used as solvent.

The addition of the mixture of silver- and zinc-salts to the mixture of a carbonate source can be carried out by placing the mixture of a carbonate source into a flask and adding the silver- and zinc-salts thereto or by placing the mixture of the silver- and zinc-salts into a flask and adding the mixture of a carbonate source thereto. Preferably the mixture of silver- and zinc-salts is added dropwise to the mixture of a carbonate source.

In a preferred embodiment the addition of the mixture of silver- and zinc-salts to the mixture of a carbonate source (step ii) is carried out at temperatures from 10 to 90° C., more preferably from 20 to 70° C., especially preferred at a temperature of 50° C.

The isolation of the co-precipitated carbonates in step (iii) is usually effected by filtration, centrifugation, decantation. The term "co-precipitation" in this context preferably means the simultaneous precipitation of silver- and zinc-carbonates formed in step (ii).

In a preferred embodiment of the invention the washing of the silver- and zinc-carbonates in step (iv) is carried out with solvents which do not dissolve the desired silver- and zinc-carbonates. The term "not dissolving" in this context preferably means dissolution of the silver- and zinc-carbonates of less than 10% by weight based on the total weight of the filter cake by room temperature. In a preferred embodiment of the invention the silver- and zinc-carbonates are washed with an aqueous solvent, preferably water. The term "washing" in this context preferably means that less than 10 ppm watersoluble salts based on the filtrate different from silver- and zinc-carbonates are present in the filtercake after the washing step with water.

In a more preferred embodiment the silver- and zinc-carbonates are subsequently washed with a non aqueous solvent. Preferred solvents are selected from the group consisting of methanol, ethanol, isopropanole, acetone, tetrahydrofurane, dioxane and mixtures thereof. Especially preferred is ethanol.

In a preferred embodiment of the invention step (v) is carried out under inert atmosphere, preferably at temperatures from 100 to 600° C. In a more preferred embodiment step (v) is carried out at temperatures from 350 to 600° C. The term "thermal decomposition" in this context preferably means the chemical reaction in which the silver- and zinc-carbonates break up into elemental silver and zinc oxide by heating.

In the following a preferred embodiment of the method for producing a composite of the invention is described in more detail without limiting the invention thereto.

In a first step a solution of at least one silver-salt is mixed with a solution of at least one zinc-salt. Afterwards the resulting solution of silver- and zinc-salts is added to a solution of potassium carbonate in water at 50° C. and the resulting silver- and zinc-carbonates are co-precipitated by filtration and washing of the carbonate mixtures with water (until the test strips indicate less than 10 ppm of nitrate in the filtercake), followed by ethanol and filtration.

In a further step the formed silver-, zinc-carbonate-mixture which preferably contains as solvent ethanol, preferably pure ethanol, is heated under inert atmosphere up to temperatures between 350-600° C. until mass loss is constant.

The process is controlled by TGA (20° C./min) and by DSC (20° C./min).

In a preferred embodiment a composite of the invention as defined in detail above is producible, more preferably produced, by a process as disclosed by the present invention.

Owing to the antimicrobial properties of the composite of the invention the use of a composite according to the present invention as an antimicrobial agent is a further object of the invention.

The composite of the invention embedded in a membrane provide a membrane surface which is resistant to microbial colonization and adhesion, and provide more easily removable foulant layers. The prevention of biofilm-formation on membrane materials used in gas separation or water processing for preparing e.g. drinking water, process water or cooling water, or improve their quality is one of the embodiments of this invention.

It is therefore a further object of the present invention to provide an antimicrobial membrane system or membrane comprising a composite of the present invention and a membrane material, preferably an organic polymer.

Besides the composite according to the present invention the antimicrobial membrane system or membrane may comprise further materials useful in combination with the composite. Such materials are known to a person skilled in the art and may include further antimicrobials, antioxidants, UV-absorbers and light stabilizers, metal desactivators, phosphites and phosphonites, hydroxylamines, nitrones, thiosynergists, peroxide scavengers, basic co-stabilizers, nucleating agents, fillers and reinforcing agents, benzofuranones and isoindolinones.

Further antimicrobials may include, for instance di- or trihalogeno-hydroxydiphenylethers such as Diclosan or Triclosan, 3,5-dimethyl-tetrahydro-1,3,5-2H-thiodiazin-2-thione, bis-tributyltinoxide, 4,5-dichlor-2-n-octyl-4-isothiazolin-3-one, N-butyl-benzisothiazoline, 10,10'-oxybisphenoxyarsine, zinc-2-pyridinthiol-1-oxide, 2-methylthio-4-cyclopropylamino-6-($\alpha,\beta$-dimethylpropylamino)-s-triazine, 2-methylthio-4-cyclopropylamino-6-tert-butylamino-s-triazine, 2-methylthio-4-ethylamino-6-($\alpha,\beta$-dimethylpropylamino)-s-triazine, 2,4,4'-trichloro-2'-hydroxydiphenyl ether, IPBC, carbendazim or thiabendazole.

Further useful additives may be selected from the materials listed below, or mixtures thereof:
1. Antioxidants:
1.1. Alkylated monophenols, for example 2,6-di-tert-butyl-4-methylphenol,
1.2. Alkylthiomethylphenols, for example 2,4-dioctylthiomethyl-6-tert-butylphenol,
1.3. Hydroquinones and alkylated hydroquinones, for example 2,6-di-tert-butyl-4-methoxy-phenol, 2,5-di-tert-butylhydroquinone,
1.4. Tocopherols, for example $\alpha$-tocopherol,
1.5. Hydroxylated thiodiphenyl ethers, for example 2,2'-thio-bis(6-tert-butyl-4-methylphenol),
1.6. Alkylidenebisphenols, for example 2,2'-methylenebis(6-tert-butyl-4-methylphenol),
1.7. O-, N- and S-benzyl compounds, for example 3,5,3',5'-tetra-tert-butyl-4,4'-dihydroxydibenzyl ether,
1.8. Hydroxybenzylated malonates, for example dioctadecyl-2,2-bis(3,5-di-tert-butyl-2-hydroxybenzyl)malonate,
1.9. Aromatic hydroxybenzyl compounds, for example 1,3,5-tris(3,5-di-tert-butyl-4-hydroxy-benzyl)-2,4,6-trimethylbenzene,
1.10. Triazine compounds, for example 2,4-bis(octylmercapto)-6-(3,5-di-tert-butyl-4-hydroxy-anilino)-1,3,5-triazine,
1.11. Benzylphosphonates, for example dimethyl-2,5-di-tert-butyl-4-hydroxybenzylphosphonate,
1.12. Acylaminophenols, for example 4-hydroxylauranilide,
1.13. Esters of $\beta$-(3,5-di-tert-butyl-4-hydroxyphenyl)propionic acid with mono- or polyhydric alcohols,
1.14. Esters of $\beta$-(5-tert-butyl-4-hydroxy-3-methylphenyl) propionic acid with mono- or poly-hydric alcohols,
1.15. Esters of $\beta$-(3,5-dicyclohexyl-4-hydroxyphenyl)propionic acid with mono- or polyhydric alcohols,
1.16. Esters of 3,5-di-tert-butyl-4-hydroxyphenyl acetic acid with mono- or polyhydric alcohols,
1.17. Amides of $\beta$-(3,5-di-tert-butyl-4-hydroxyphenyl)propionic acid e.g. N,N'-bis(3,5-di-tert-butyl-4-hydroxyphenyl-propionyl)hexamethylenediamide,
1.18. Ascorbic acid (vitamin C),
1.19. Aminic antioxidants, for example N,N'-di-isopropyl-p-phenylenediamine.
2. UV absorbers and light stabilizers:
2.1. 2-(2'-Hydroxyphenyl)benzotriazoles, for example 2-(2'-hydroxy-5'-methylphenyl)-benzo-triazole,
2.2. 2-Hydroxybenzophenones, for example the 4-hydroxy derivatives,
2.3. Esters of substituted and unsubstituted benzoic acids, for example 4-tert-butyl-phenyl salicylate,
2.4. Acrylates, for example ethyl $\alpha$-cyano-$\beta,\beta$-diphenylacrylate,
2.5. Nickel compounds, for example nickel complexes of 2,2'-thio-bis[4-(1,1,3,3-tetramethyl-butyl)phenol],
2.6. Sterically hindered amines, for example bis(2,2,6,6-tetramethyl-4-piperidyl)sebacate.
2.7. Oxamides, for example 4, 4'-dioctyloxyoxanilide,
2.8. 2-(2-Hydroxyphenyl)-1,3,5-triazines, for example 2,4-bis(2,4-dimethylphenyl)-6(2-hydroxy-4-octyloxyphenyl [or -4-dodecyl/tridecyloxyphenyl])-1,3,5-triazine.
3. Metal deactivators, for example N,N'-diphenyloxamide.
4. Phosphites and phosphonites, for example triphenyl phosphite.
5. Hydroxylamines, for example N,N-dibenzylhydroxylamine.
6. Nitrones, for example, N-benzyl-alpha-phenylnitrone.
7. Thiosynergists, for example dilauryl thiodipropionate.
8. Peroxide scavengers, for example esters of $\beta$-thiodipropionic acid.
9. Basic co-stabilizers, for example melamine, polyamides, polyurethanes, alkali metal salts and alkaline earth metal salts of higher fatty acids, for example calcium stearate, zinc stearate.
10. Nucleating agents, for example inorganic substances, such as talcum, metal oxides.
11. Fillers and reinforcing agents, for example calcium carbonate, silicates, glass fibres, glass beads, asbestos, talc, kaolin, mica, barium sulfate, metal oxides and hydroxides, carbon black, graphite, wood flour and flours or fibers of other natural products, synthetic fibers.
12. Other additives, for example plasticisers, lubricants, emulsifiers, pigments, rheology additives, catalysts, flow-control agents, optical brighteners, flameproofing agents, antistatic agents and blowing agents.
13. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839, EP-A-0591102; EP-A-1291384.

For more details on useful stabilizers and additives, see also list on pages 55-65 of WO 04/106311, which is hereby incorporated by reference.

The membrane system may further comprise hydrophilicity enhancing additives, such as those disclosed in WO 02/042530.

The amount of the composite of the present invention in the membrane system according to the present invention is preferably 0.05 to 20 weight percent, more preferably 0.05 to 10 weight percent, based on the total weight of the polymer. The weight ratio of the further additives to the composite within the membrane system of the invention is preferably in the range of 5:95 to 95:5.

The composite of the invention may be added to the polymer composition forming the membrane system or membrane. A film is formed in which the composite of the invention is dispersed, mainly at the surface. Incorporation of the composite may advantageously be effected by addition of the composite to the polymeric casting solution. The membrane system or membrane may be formed after immersion of said solution in a coagulation bath (mainly water).

A preferred embodiment to prepare a membrane system or membrane of the invention constitutes the formation of a continuous film having microstructural characteristics of ultrafiltration membranes by a membrane solution including Polyethersulfone, Polyvinylpyrolidon as pore former, a composite of the invention and any other additives commonly used in membrane preparation;

The membrane system or membrane of the invention is capable of significantly reducing biofilm growth compared to the same membrane system or membrane not containing the substantially water insoluble silver/zinc oxide-based composite of the invention. Closed water systems (water purification, desalination) using e.g. plastic parts such as pipes, filters, valves or tanks can be subject to bacterial or algal colonization and biofilm formation, leading to serious damages of filter efficacy, such as membrane permeability (flow rate), and followed by deterioration of the materials and contamination of the circuit liquids.

Other problems with said surfaces can derive from algal or bacterial biofilm formation resulting in an undesired change in their hydrodynamic properties and affecting e.g. the flowrate in pipes, or also the trouble-free use of boats, marine or other limnological applications.

The specific composite of the invention provides membrane systems or membranes with particular mechanisms for durable enhancement of antimicrobial properties of the membrane system or membrane. The antimicrobial membrane systems or membranes include a polymeric material and a composite of the invention, which is incorporated into and either homogeneously distributed throughout the polymeric material or dispersed in the polymeric material near its surface.

Antimicrobial membrane systems or membranes of the invention may be prepared from organic polymers, e.g. as commonly listed in WO04/106311 page 48, bottom paragraph, until page 54 (item 29). Preferred polymers are selected from the group consisting of cellulose acetates, polyacrylonitriles, polyamides, polyolefines, polyesters, polysulfones, polyethersulfones, polycarbonates, polyether ketones, sulfonated polyether ketones, polyamide sulfones, polyvinylidene fluorides, polyvinylchlorides, polystyrenes and polytetrafluorethylenes or mixtures thereof. Even more preferred polymers are selected from the group consisting of polysulfones, polyethersulfones, polyvinylidene fluorides, polyamides, cellulose acetate and mixtures thereof.

The amount of the composite according to the invention in the membrane of the invention is preferably 0.05-20% by weight, more preferably 0.05-10% by weight, based on the total weight of the organic polymer.

The process of antimicrobial membrane preparation often follows the steps as outlined below:

In a first step the organic polymers are dissolved in an organic solvent, such as N-methyl pyrrolidone, dichloromethane, dimethylformamide (DMF), dimethylacetamide, etc. or a suitable solvent mixture, e.g. mixture of these. Other common solvents are found in the literature. In a second step the composite of the invention is added to the fraction of solvent and is well dispersed, e.g. using ultrasonic mixer or any other suitable mixing devices. In a third step the slurry is dispersed throughout the polymer solution, e.g. using a mechanical stirrer at optimum speed. In a fourth step other additives (mainly organic and/or polymeric such as listed above, e.g. pore formers and/or hydrophilic additives) commonly used in membrane compositions may be added to the mixture of the composite of the invention and polymer. In a fifth step the resulting solution is cast into a thin film membrane by known methods resulting in a semi permeable or dense membrane with dispersed composite of the invention at least on one side of membrane. Alternatively, in the fifth step the resulting solution is metered into a non-solvent of the polymers where the polymers precipitate in a controlled way to form a semipermeable or dense membrane with the dispersed composite of the invention. Further alternatives of membrane preparation are track-etching, stretching, leaching, interfacial polymerization, sintering, sol-gel processes, adding an active membrane layer, grafting and sputter deposition.

The membrane may be used as a stand alone membrane or may be cast on a support to make a composite membrane. Often used are semi-permeable membranes.

In a preferred embodiment the water processing is carried out in a membrane system.

The membranes, mostly prepared of organic polymer materials, may be those known for reverse osmosis, ultrafiltration, nanofiltration, gas separation, pervaporation and/or microfiltration.

They may be cast as a stand alone film or cast on a support film or membrane in the fabrication of composite membranes and may have flat sheet, fine hollow fiber, capillary, spiral wound, tubular, or plate and frame configuration.

Furthermore, they may be either asymmetric or symmetric. Asymmetric membranes have pore sizes on one face of the membrane that are different from the pore size on the other face. Symmetric membranes have equal pore sizes on either face.

The treatment of the membrane materials (before the membrane is formed) or membranes (finished structure) with the present composite comprises e.g. the incorporation into the membrane material or the membrane structure or into the surface (coating) of the membrane. Said incorporation includes e.g. precipitation or moulding (extrusion) processes. The composite of the invention is generally well fixed within the polymeric material, i.e. it is as a rule non-leachable. The composite of the invention is preferably added as such.

The membrane system usually comprises at least one cast semi-permeable or dense membrane having a polymeric structure and the controlled release/slow leaching composite of the invention incorporated into the polymeric material and dispersed throughout said material or, optionally, in a coating layer.

The preparation of the semipermeable or dense membranes comprising the composite of the invention is generally known in the art.

Cellulose acetate membranes are cast e.g. from a composite solution (dope solution) containing e.g. a mixture of cellulose di- and -triacetate and the composite of the invention in an amount as indicated above on a support (fabric). The solvent used is e.g. a dioxane/acetone mixture wherein also the composite of the invention is readily soluble. They may be cast on a support (polyester fabric) and are allowed to precipitate at lower temperatures.

In the preparation of hollow fiber membranes from e.g. polyacrylonitriles polysulfones, polyether sulfones, polyether ketones, polyvinylidene fluorides or sulfonated polyvinylidene fluorides the solvents used are e.g. aprotic solvents such as dimethylformamide, dimethylsulfoxide, dimethylacetamide, N-methylpyrrolidone and mixtures thereof.

The composite of the invention is readily dispersable in said solvents or solvent mixtures and will precipitate with the polymer when a non-solvent comes into contact with the dope solution, e.g. by passing the dope solution through a spinneret to form the hollow fiber. Composite membranes, such as composite polyamide membranes, may be prepared by casting a dope solution of a polysulfone and the composite of the invention onto a reinforcing fabric (polyester). When coming into contact with water, the polysulfone and the composite of the invention precipitate onto the reinforcing fabric and form a film. After drying this polysulfone film (membrane) is then soaked with an organic carboxylic chloride solution followed by aqueous amine solution, so that a polyamide layer is formed on the polysulfone membrane. After drying a composite membrane for reverse osmosis is obtained.

In an alternative embodiment of the present invention the membrane system may be furnished with antimicrobial properties by rinsing the whole system (membranes, pipes, tanks etc.) with a rinsing liquor containing 0.01 to 2.0% of the composite of the invention, based on the weight of the liquor. The composite of the invention are normally substantive to the polymeric material of the membrane (filtration) system, and by diffusing into the top layer (e.g. coatings) of the polymeric material a long lasting protection against biofilm growth and bacterial and algal decay can be achieved.

The rinsing method is also suitable to reactivate antimicrobial activities of antimicrobially exhausted membrane filtration systems.

Preferably, the rinsing liquor is an aqueous formulation containing besides the composite of the invention conventional components like surfactants, which may be non-ionic, anionic or zwitter-ionic compounds, sequestering agents, hydrotropes, alkali metal hydroxides (sources of alkalinity), preservative, fillers, dyes, perfumes and others. The components and their use in rinsing liquors are well known to those skilled in the art.

The composites of the invention is very efficacious in preventing the growth of almost all kinds of bacteria present in water, have slow, controlled leaching, are safe and non-toxic to human and animal skin, and show good bio-degradability and altogether a more favorable ecological profile in the aquatic environment when compared with e.g. trichloro-hydroxydiphenylethers which are also used as antimicrobials.

The membrane system of the invention is particularly useful in desalination, membrane bioreactors and other aqueous purification processes. The membranes may be semi-permeable membranes, as commonly used in conventional filtration processes, or dense membranes as used, for example, in reverse osmosis processes.

It is thus a further object of the present invention to use the membrane system of the invention for the filtration of aqueous liquids or aqueous dispersions, e.g. selected from liquid food, beverages, pharmaceuticals and pre-products thereof. They may further be used for:
gas separation,
the separation of bio-molecules or bio-particles, e.g. blood-platelets or bio-polymers of high molecular weight such as proteins, from aqueous liquids or dispersions in biotechnology or medicine,
the filtration of water used in power generation,
the purification and/or decontamination of water for industrial processes, chemical processes, metal treatment, semiconductor processing, pulp and paper processing, and especially of drinking water and/or waste water. A subject of specific interest is a reverse osmosis membrane system comprising the present composite particles, as advantageously used in desalination processes e.g. for the production of drinking water from sea water.

Another application is the use of the membrane system in water reuse applications (RO, NF, MF etc) where microbial growth occurs on the membrane, even with relatively "clean" water, and causes fouling.

The following test methods and examples are for illustrative purposes only and are not to be construed to limit the instant invention in any manner whatsoever. Room temperature (r.t.) depicts a temperature in the range of 20-25° C.; over night denotes a time period in the range of 12-16 hours. Percentages are by weight unless otherwise indicated. The particle size distribution was measured by laser granulometry: apparatus: Mastersizer 2000 by Malvern. The analysis of the particle size distribution was done according to the Fraunhofer Diffraction Method.

According to the present invention the method to be used to determine the primary particle size is the energy dispersive X-ray spectroscopy (SEM/EDX; instrument: REM: Quantum 200 FEI with field emitter (FEG); max 30 kV; REM picturing with ETD (SE-Detector) and SSD (BSE-Detector) at 10 kV (e-acceleration voltage). Silver occurs enlightened due to its higher atomic number compared to zinc oxide; this observation was also validated by EDX measurements.
Abbreviations used in the examples:
Materials Used
  Silver nitrate: commercial product from Aldrich, Germany.
  Zinc nitrate: commercial product from Aldrich, Germany.
  Potassium carbonate: commercial product from Aldrich, Germany.
  Nitrate test strips: commercial product from Merck, Germany.
  N-methylpyrolidone (NMP): commercial product from Aldrich, Germany.
  Polyvinylpyrrolidone (PVP): Luvitec® PVP 30 K commercial product from BASF, Germany.
  Poylethersulfone (PES): Ultrason® 2020 PSR commercial product from BASF, Germany.
  *E. coli*: *Escherichia coli*
  *S. aureus*: *Staphylococcus aureus*

EXAMPLE 1

Preparation of Ag/ZnO Composite

Co-precipitation of the Carbonates

Zinc nitrate (59.5 g; 0.2 mol) and silver nitrate (6.4 g; 0.04 mol) are dissolved in 100 ml deionized water at 50° C. This solution is added drop wise within 30 min to a stirred (8000 rpm) solution of potassium carbonate (34.8 g; 0.22 mol) in 300 ml water at 50° C. (1000 ml beaker, which was darkened by aluminium foil). For stirring an Ultraturax T25 (Company: IKA) is used. After stirring for 30 min a light yellow suspension is formed.

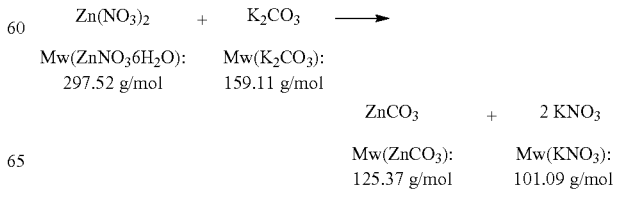

$$2\,AgNO_3 + K_2CO_3 \longrightarrow$$

Mw(AgNO$_3$): 169.87 g/mol  
Mw(K$_2$CO$_3$): 159.11 g/mol $$Ag_2CO_3 + 2\,KNO_3$$

Mw(Ag$_2$CO$_3$): 275.74 g/mol  
Mw(KNO$_3$): 101.09 g/mol

The suspension was filtered in a Buechner funnel (Filter type: Whatman® Sort 1: middle retention and flux. Particle retention 11 μm, filtration velocity (Herzberg) 150 s, weight 88 g/m², thickness 0.18 mm, ash 0.06%) and washed two times with deionized water until less than 10 ppm nitrate is found in the filtrate (Merck: Nitrate test strip). Typically one needs 20 l/kg precipitate. The filter cake (30 g) is dispersed in ethanol (100 ml) and filtered again. The filter cake contains 100 w % ethanol to metal carbonates after filtration.

Drying and Calcination

The filter cake was dried at 200° C. at 1013 mbar for 40 min while increasing the temperature to 350° C. Calcination was carried out at 350° C. for 90 min. Completion of calcination was gravimetrically dedicated until theoretically mass balance was achieved (Mass loss: Found: 24.3 w %, calculated 30.3 w %)

$$ZnCO_3 \xrightarrow{>300°\,C.} ZnO + CO_2$$

Mw(ZnCO$_3$): 125.37 g/mol  
Mw(ZnO): 81.37 g/mol  
Mw(CO$_2$): 44.02 g/mol $$Ag_2CO_3 \xrightarrow{200°\,C.} Ag_2O + CO_2$$

Mw(Ag$_2$CO$_3$): 275.74 g/mol  
Mw(Ag$_2$O): 231.74 g/mol  
Mw(CO$_2$): 44.02 g/mol $$2\,Ag_2O \xrightarrow{>100;\,300°\,C.} 4\,Ag + O_2$$

Mw(Ag$_2$O): 231.74 g/mol  
Mw(Ag$_2$O): 107.87 g/mol  
Mw(O): 16 g/mol

Process control by TGA (20° C./min): three peaks of mass loss are found: 155° C.; 237° C.; 350° C. Process control by DSC (20° C./min): two peaks of thermal activity: 170° C. (−26 J/g); 248° C. (191 J/g)

Appearance: brown powder

Silver content: 19.2 wt %

Ag particle size by EDX: 60 nm±15 nm

ZnO particle size by EDX: <20 μm

Particle size distribution by laser granulometry: 5.7 μm (50% probability; fluid: 0.08% Na-Citrate)

BET surface [m²/g]: 38

COMPARATIVE EXAMPLE 1

Silver nitrate (10.0 g, 0.059 mol) is dissolved in 150 ml water at 50° C. in a 300 ml Erlenmeyer tube. Then zinc oxide is added in one portion. The suspension was homogenized by a Ultraturax® T25 stirrer for 10 min. The sodium chloride (3.4 g, 0.059 mol) was dissolved in 50 ml water. The brine was added to the stirred suspension in 5 min forming silver chloride. Subsequently, the reaction mixture was stirred for 30 min at 50° C.

$$AgNO_3 + NaCl \longrightarrow AgCl + 2\,NaNO_3$$

Mw(AgNO$_3$): 169.87 g/mol  
Mw(NaCl): 58.43 g/mol  
Mw(AgCl): 143.25 g/mol  
Mw(NaNO$_3$): 84.98 g/mol $$y\,ZnO + x\,AgCl \longrightarrow [AgCl]_x \cdot [ZnO]_y$$

Mw(ZnO): 81.37 g/mol  
Mw(AgCl): 143.25 g/mol $$4\,AgCl \cdot ZnO + N_2H_4 \cdot H_2O \longrightarrow$$

Mw(N$_2$H$_4$·H$_2$O): 50.05 g/mol $$4\,Ag \cdot ZnO + 4\,HCl + N_2 + H_2O$$

Mw(HCl): 36.45 g/mol $$ZnO + HCl \longrightarrow ZnCl_2 + H_2O$$

Mw(ZnO): 81.37 g/mol  
Mw(HCl): 36.45 g/mol  
Mw(ZnCl$_2$): 136.27 g/mol

Then hydrazine hydrate (3.0 g, 0.06 mol) was dropped to the suspension.

Thereby the colour changes from white to beige-brown. The suspension was filtered and the filter cake was washed with 100 ml water. In the next step ethanol (100 ml) was added and washed again. Finally all volatile compounds where removed in a vacuum oven at 130° C.

Yield: 31.0 g, 99% of theory

Appearance: brown powder

Silver content: 19.7 wt %

Ag particle size by EDX: 200 nm

ZnO particle size by EDX: <2 μm

Particle size distribution by laser granulometry: 1.1 μm (50% probability; fluid: 0.08% Na-Citrate)

BET surface [m²/g]: 7.6

COMPARATIVE EXAMPLE 2

As comparative compound Hygentic® 400 (commercial product from Ciba, Switzerland) was used, which consists of 100% elemental silver.

EXAMPLE 2

Testing of Antibacterial Activity of Ag/ZnO Composite

| Test method: | CG 161/European Standard method EN 1040 |
|---|---|
| Test organisms (inoculum) | Overnight culture [cfu/mL] |
| E. coli ATCC 10536 | 2.9 × 10⁸ |
| S. aureus ATCC 3865 | 2.3 × 10⁸ |
| Inoculum concentration in the test: 10⁷ cfu/mL | |
| Contact times at 22° C.: | 5 min; 30 min |
| Incubation: | |
| S. aureus | 24 h |
| E. coli | 24 h |

Inactivation: TSB Special

The colony count of the inoculum was retrieved after incubation. The inactivation of the test substances was satisfactory with TSB.

Test concentration in the suspension test: 0.1% and 1% total silver

Test samples:

| | |
|---|---|
| 1% test sample: | 0.535 g test substance: Ex. 1 (18.7% silver) |
| | ad 9 g H2O |
| | 1 mL inoculum |
| 0.1% test sample: | 0.054 g test substance: Ex. 1 (18.7% silver) |
| | ad 9 g H2O |
| | 1 mL inoculum |
| 1% test sample: | 0.508 g test substance: Comp. Ex. 1 (19.7% silver) |
| | ad 9 g H2O |
| | 1 mL inoculum |
| 0.1% test sample: | 0.051 g test substance: Comp. Ex. 1 (19.7% silver) |
| | ad 9 g H2O |
| | 1 mL inoculum |
| 1% test sample: | 0.1 g test substance: Comp. Ex. 2 (100% silver) |
| | ad 9 g H2O |
| | 1 mL inoculum |
| 0.1% test sample: | 0.01 g test substance: Comp. Ex. 1 (100% silver) |
| | ad 9 g H2O |
| | 1 mL inoculum |

Results: cfu/sample JIS Z 2801

TABLE 1

| Sample | S. aureus cfu/mL | log reduction 5 min. | log reduction 30 min. | E. coli cfu/mL | log reduction 5 min. | log reduction 30 min. |
|---|---|---|---|---|---|---|
| Inoculum | 2.30E+08 | | | 2.2E+08 | | |
| H2O reference 5' | 2.80E+07 | | | 1.30E+07 | | |
| H2O reference 30' | 3.40E+07 | | | 1.50E+07 | | |
| Ex. 1 0.1% | <100 | >5 | | <100 | >5 | |
| | <100 | | >5 | <100 | | >5 |
| Ex. 1 1% | 1.00E+04 | 3.4 | | <100 | >5 | |
| | <100 | | >5 | <100 | | >5 |
| Comp. Ex. 1 0.1% | 1.90E+07 | <1 | | 7.20E+06 | <1 | |
| | 2.00E+07 | | <1 | 3.60E+05 | | 1.6 |
| Comp. Ex. 1 1% | 1.60E+07 | <1 | | <100 | >5 | |
| | 1.90E+07 | | <1 | <100 | | >5 |
| Comp. Ex. 2 0.1% | 2.07E+07 | <1 | | <100 | >5 | |
| | 7.11E+02 | | 4.6 | <100 | | >5 |
| Comp. Ex. 2 1% | <100 | >5 | | <100 | >5 | |
| | <100 | | >5 | <100 | | >5 |

EXAMPLE 3

Preparation of Membrane

N-methylpyrolidone (NMP) (70 ml) was placed in a three-neck flask with agitator. Polyvinylpyrolidone Luvitec® PVP 40 K (6 g) was added to the NMP and the temperature increased to 60° C. and stirred until a homogeneous clear solution was obtained. The required level of composite of the invention (concentration given in ppm silver in respect to PES; cf. table 2) was mixed to 6 g of NMP and sonicated for 20 minutes and the suspension was added to the PVP solution and stirred until the solution was homogeneous. Polyethersulfone Ultrason® 2020 PSR (18 g) was added to the solution and stirred until a viscous solution was obtained. The solution was degassed overnight at room temperature (30-40° C.). The membrane solution was reheated to 70° C. The membrane was casted on the glass with a casting knife at room Temperature and allowed to dry for 30 seconds before immersion. The membrane is casted into a water bath of 25° C. After 10 minutes of immersion, the membrane is rinsed with hot water (65-75° C., 30 minutes).

EXAMPLE 4

Testing of Antibacterial Activity of Membrane

| | |
|---|---|
| Test method: | JIS Z 2801 (Japanese Standard method) |
| Test strain: | E. coli ATCC 10536 |
| | S. aureus ATCC 3865 |
| Contact time/Temp | 24 hours at 37° C. (JIS Z 2801) |
| Sample size | 2.5 × 2.5 cm |
| Cover film size | 2 × 2 cm |
| Inoculum | 100 µL of the cell suspension |

Sample handling: After incubation of inoculated samples for 24 h the whole liquid was drawn in the material and for the elution of cells the samples were transferred into "Stomacher bags" filled with 10 ml inactivation buffer and "kneaded" for 1 minute.

The following membrane samples were prepared according to the procedure of example 3 containing different composite contents with variable silver contents as listed in table 2. Testing was conducted against *Escherichia coli* and *Staphylococcus aureus* according to the test method described above.

Results: cfu/sample JIS Z 2801

TABLE 2

| Membrane | Formulation | Initial composite content to PES [w %] | Initial Zn content to PES [ppm] | Initial Ag content to PES [ppm] | E. coli ATCC 10536 cfu/sample | S. aureus ATCC 6538 cfu/sample |
|---|---|---|---|---|---|---|
| Ex. 3A | Blank control 0 h | 0 | 0 | 0 | 5.6E+05 | 9.6E+05 |
| Ex. 3B | Blank control 24 h | 0 | 0 | 0 | 8.0E+05 | 2.5E+05 |
| | | | | | 1.9E+05 | 5.6E+05 |
| Ex. 3C | ZnO | 0.03 | 241 | 0 | 210 | 3.7E+04 |
| | | | | | 6.6E+04 | 1.8E+05 |
| Ex. 3D | ZnO | 0.08 | 643 | 0 | <10 | 4.1E+02 |
| | | | | | <10 | 1.3E+04 |
| Ex. 3E | 40% Ag/ZnO | 0.05 | 241 | 200 | <10 | <10 |
| | | | | | <10 | <10 |
| Ex. 3F | 40% Ag/ZnO | 0.5 | 2410 | 2000 | <10 | <10 |
| | | | | | <10 | <10 |
| Ex. 3G | 40% Ag/ZnO | 0.5 | 2410 | 2000 | <10 | <10 |
| | | | | | <10 | 440 |
| Ex. 3H | 20% Ag/ZnO | 1.0 | 6427 | 2000 | <10 | <10 |
| | | | | | <10 | <10 |

TABLE 2-continued

| Membrane | Formulation | Initial composite content to PES [w %] | Initial Zn content to PES [ppm] | Initial Ag content to PES [ppm] | E. coli ATCC 10536 cfu/sample | S. aureus ATCC 6538 cfu/sample |
|---|---|---|---|---|---|---|
| Ex. 3I | 40% Ag/ZnO | 2.5 | 12051 | 10000 | <10<br><10 | <10<br><10 |
| Ex. 3J | 40% Ag/ZnO | 5.0 | 24101 | 20000 | <10<br><10 | <10<br><10 |
| Ex. 3K | 20% Ag/ZnO | 5.0 | 32135 | 10000 | <10<br><10 | <10<br><10 |
| Ex. 3L | 20% Ag/ZnO | 10.0 | 64269 | 20000 | <10<br><10 | <10<br><10 |

The invention claimed is:

1. A composite comprising
(a) 10.1-99.9% by weight of elemental Ag and
(b) 0.1-89.9% by weight of ZnO,
wherein the sum of (a) and (b) makes 90% or more by weight of the composite and wherein the elemental Ag has a primary particle size of 10-200 nm and the ZnO has a primary particle size of 0.1 to below 50 μm and the composite has a particle size distribution of 0.1-50 μm and a BET surface area of 10-100 m$^2$/g.

2. Composite according to claim 1, wherein the elemental Ag has a primary particle size of 10-100 nm and/or the ZnO has a primary particle size of 0.1 to below 30 μm and/or the composite has a particle size distribution of 1-30 μm and/or a BET surface area of 20-80 m$^2$/g.

3. Composite according to claim 1, wherein the elemental Ag has a primary particle size of 30-80 nm and/or the ZnO has a primary particle size of 0.1 to below 22 μm and/or the composite has a particle size distribution of 1-22 μm and a BET surface area of 35-45 m$^2$/g.

4. Composite according to claim 1 comprising
(a) 20.1-99.9% by weight of elemental Ag and
(b) 79.9-0.1% by weight of ZnO.

5. Composite according to claim 1 prepared by a process comprising
(i) mixing a first mixture of at least one Ag-salt with a second mixture of at least one Zn-salt thereby forming a third mixture of Ag- and Zn-salts,
(ii) adding the third mixture to a mixture of a carbonate source,
(iii) co-precipitating of the Ag- and Zn-carbonates formed in step (ii),
(iv) washing of the Ag- and Zn-carbonates and
(v) thermal decomposition of the Ag- and Zn-carbonates.

6. The composite according to claim 5, where in step (i) the Ag-salt is selected from the group consisting of Ag-nitrate, Ag-acetate, Ag-sulfate, Ag-citrate, Ag-methanesulfonate, Ag-fluoride and mixtures thereof and/or the Zn-salt is selected from the group consisting of Zn-nitrate, Zn-acetate, Zn-sulfate, Zn-citrate, Zn-methanesulfonate, Zn-chloride, Zn-bromide, Zn-iodide and mixtures thereof.

7. The composite according to claim 5, wherein the carbonate source used in step (ii) is selected from the group consisting of carbonate acid, ammonium carbonate, guadinium carbonate, potassium carbonate, sodium carbonate, lithium carbonate, corresponding hydrogen carbonates thereof and mixtures thereof.

8. The composite according to claim 5, wherein
(a) step (ii) is carried out at temperatures from 10 to 90° C. and/or
(b) step (v) is carried out under inert atmosphere at temperatures from 100 to 600° C.

9. Antimicrobial membrane comprising a composite according to claim 1 and an organic polymer.

10. Antimicrobial membrane according to claim 9, wherein the organic polymer is selected from the group consisting of cellulose acetates, polyacrylonitriles, polyamides, polyolefines, polyesters, polysulfones, polyethersulfones, polycarbonates, polyether ketones, sulfonated polyether ketones, polyamide sulfones, polyvinylidene fluorides, polyvinylchlorides, polystyrenes, polytetrafluorethylenes and mixtures thereof.

11. Antimicrobial membrane according to claim 9, wherein the amount of the composite is 0.05-20% by weight, based on the weight of the organic polymer.

12. Composite according to claim 1 comprising
(a) 20.1-40.0% by weight of elemental Ag and
(b) 79.9-60.0% by weight of ZnO.

13. The composites according to claim 5 wherein the carbonate source is potassium carbonate.

14. Antimicrobial membrane according to claim 9 wherein the organic polymer is selected from the group consisting of polysulfones, polyethersulfones, polyvinylidene fluorides, polyamides, cellulose acetate and mixtures thereof.

* * * * *